(12) United States Patent
Kwan et al.

(10) Patent No.: US 7,245,378 B2
(45) Date of Patent: *Jul. 17, 2007

(54) MEASURING LASER LIGHT TRANSMISSIVITY IN A TO-BE-WELDED REGION OF A WORK PIECE

(75) Inventors: Kin-Ming Kwan, Lexington, KY (US); Jonathan H. Laurer, Lexington, KY (US); David T. Shadwick, Versailles, KY (US); Audrey D. Rodgers, Lawrenceburg, KY (US)

(73) Assignee: Lexmark International, Inc., Lexington, KY (US)

( * ) Notice: Subject to any disclaimer, the term of this patent is extended or adjusted under 35 U.S.C. 154(b) by 138 days.

This patent is subject to a terminal disclaimer.

(21) Appl. No.: 11/228,750

(22) Filed: Sep. 16, 2005

(65) Prior Publication Data

US 2006/0012792 A1    Jan. 19, 2006

Related U.S. Application Data

(60) Continuation of application No. 11/093,971, filed on Mar. 30, 2005, now Pat. No. 6,980,296, which is a division of application No. 10/359,470, filed on Jan. 30, 2003, now abandoned.

(51) Int. Cl.
  *G01N 21/00* (2006.01)
(52) U.S. Cl. ............... 356/432; 356/239.7; 219/121.63; 219/121.64; 250/559.29
(58) Field of Classification Search ........ 356/431–444, 356/239.7; 250/559.29, 559.36, 559.33; 219/121.63, 121.64, 121.83, 121.61, 121.62, 219/121.84, 121.85; 382/151–152, 141, 382/145, 148–149

See application file for complete search history.

(56) References Cited

U.S. PATENT DOCUMENTS

| | | | |
|---|---|---|---|
| 3,769,117 A | 10/1973 | Bowen et al. | |
| 4,434,350 A | 2/1984 | Flisikowski et al. | |
| 4,636,609 A | 1/1987 | Nakamata | |
| 4,663,513 A | 5/1987 | Webber | |
| 4,694,153 A | 9/1987 | Bejczy et al. | |
| 5,038,016 A | 8/1991 | Robertson et al. | |
| 5,045,668 A * | 9/1991 | Neiheisel et al. | 219/121.83 |
| 5,045,669 A | 9/1991 | Ortiz | |
| 5,272,312 A | 12/1993 | Jurca | |
| 5,329,133 A | 7/1994 | Uesugi et al. | |
| 5,450,113 A | 9/1995 | Childers et al. | |
| 5,681,490 A | 10/1997 | Chang | |
| 5,685,074 A | 11/1997 | Pan et al. | |
| 5,698,120 A | 12/1997 | Kurozawa et al. | |

(Continued)

FOREIGN PATENT DOCUMENTS

EP        0159169       10/1985
JP        10085973 A  *  4/1998

*Primary Examiner*—Sang H. Nguyen
(74) *Attorney, Agent, or Firm*—King & Schickli, PLLC

(57) ABSTRACT

Methods for measuring laser light transmissivity of a specific position in a work piece prior to the work piece undergoing laser welding at the specific position with a laser beam having a specific welding wavelength. To obtain a baseline measurement reading, a laser light source projects a laser beam at the welding wavelength directly into a detector. Thereafter, the work piece becomes suspended between the laser light source and detector whereby an output of the detector now corresponds to a work piece measurement reading. Differences between the two readings reveal whether the work piece will yield a satisfactory weld at the specific position when later welded by a laser beam at the welding wavelength. Preferred work pieces include inkjet printhead lids and bodies.

15 Claims, 7 Drawing Sheets

U.S. PATENT DOCUMENTS

| | | |
|---|---|---|
| 5,808,641 A | 9/1998 | Miyagawa et al. |
| 5,847,356 A | 12/1998 | Santhanam |
| 5,893,959 A | 4/1999 | Muellich |
| 6,072,148 A | 6/2000 | Azdasht |
| 6,132,025 A | 10/2000 | Baughman et al. |
| 6,161,927 A | 12/2000 | Long et al. |
| 6,236,015 B1 | 5/2001 | Akhavin et al. |
| 6,292,584 B1 * | 9/2001 | Dulaney et al. ............ 382/151 |
| 6,329,629 B1 | 12/2001 | Grewell |
| 6,339,207 B1 | 1/2002 | Bishop |
| 6,396,579 B1 | 5/2002 | Hayamizu et al. |
| 6,397,465 B1 | 6/2002 | Ahkavin et al. |
| 6,531,675 B2 | 3/2003 | Faitel |
| 6,770,899 B2 | 8/2004 | Hasegawa et al. |
| 6,897,958 B2 * | 5/2005 | Yamaguchi et al. ........ 356/431 |
| 2002/0014476 A1 | 2/2002 | Tsukamoto et al. |
| 2004/0095448 A1 | 5/2004 | Buchanan et al. |

* cited by examiner

MEASURING LASER LIGHT TRANSMISSIVITY IN A TO-BE-WELDED REGION OF A WORK PIECE

This application claims priority as a continuation application of U.S. application Ser. No. 11/093,971 filed on Mar. 30, 2005 now U.S. Pat. No. 6,980,296, entitled "Measuring Laser Light Transmissivity in a To-Be-Welded Region of a Work Piece," in turn claiming priority as a division of an application by the same name having Ser. No. 10/359,470 and filed on Jan. 30, 2003 now abandoned.

FIELD OF THE INVENTION

The present invention relates to measuring light transmissivity of a work piece. In particular, it relates to measuring laser light transmissivity of a specific position in a work piece prior to the work piece undergoing laser welding at that specific position. Even more particularly, it relates to assessing whether the work piece will yield a satisfactory weld at the specific location when welded by a laser beam irradiated at a specific welding wavelength. Work pieces may comprise inkjet printhead lids and bodies.

BACKGROUND OF THE INVENTION

The art of measuring light transmissivity in a work piece is relatively well known. In general, light from a source passes from a front side of the work piece to the backside where a detector collects it. The difference between the light irradiated towards the work piece and the light that actually passes through the work piece, as collected by the detector, corresponds to the work piece transmissivity.

Problems arise, however, because the light source, often a white light source, illuminates the front of the work piece with multiple wavelengths while the detector only collects light at its tuned wavelength. This can unnecessarily limit measurement of multiple wavelengths to incorporating multiple detectors. Additionally, typical commercial transmissivity measurement devices lack sufficient irradiation power to penetrate work pieces and project light to backside detectors when the work pieces embody other than visibly clear compositions. Traditional visibly clear compositions include glass, quartz, polycarbonate, polystyrene, and the like. They usually also lack sufficient power to project light through work pieces, such as high impact polystyrene and polyester having typically low transmissivity characteristics.

Accordingly, the arts for measuring light transmissivity desire solutions for overcoming the aforementioned and other problems.

Numerous reasons exist for understanding light transmissivity in a work piece. For example, consider instances when two work pieces undergo laser welding. As background, first and second work pieces become welded to one another by way of a fixed or sweeping irradiated beam of laser light. As is known, the beam passes through the first work piece, which is transparent to laser light, where it gets absorbed by the second work piece, which is laser light absorbent. As the beam irradiates, the weld interface heats-up which causes the adjoining surfaces of the work pieces to melt. Upon cooling, the two work pieces meld together as one.

Yet, if the first work piece prevents sufficient amounts of laser light from reaching the weld interface, poor welding (underweld) results. Further, if the first work piece absorbs too much energy, the first work piece may overheat and/or suffer material degradation potentially causing poor weld appearance or unsatisfactory welds. Numerous parameters contribute to the absorption and transmission characteristics of a work piece including, but not limited to, laser wavelength, incident angle of the laser beam during welding, surface roughness of the work piece, temperature of the work pieces, thickness/dimensions of the work piece, composition of the work piece and, in instance when work pieces comprise plastics, additives such as flame retardants, plasticizers, fillers and colorants.

When the material properties and laser properties become fixed in a given system, however, the transmission rate of the laser through a work piece follows the well known Beer-Lambert Law, specifically: $I/Io=e^{(-sx)}$; where Io is the intensity of the light source incident on the work piece, I is the intensity of the light after passing through the work piece, x is the thickness of the work piece, and s is the total extinction coefficient which, in turn, is the work piece light scattering coefficient plus the work piece light absorption coefficient. Accordingly, the transmissivity of the work piece constitutes an important variable (underscored by the ratio $I/I_o$) in light transmission rates.

As such, those skilled in the laser welding arts will appreciate that having an ability to assess, predict or otherwise identify a laser light transmissivity characteristic of a work piece before the piece undergoes welding will likely significantly decrease failure weld-rates in to-be-welded work pieces.

Accordingly, a need exists in the laser welding arts for efficaciously predicting and identifying laser light transmissivity in to-be-welded regions of a work piece.

Regarding the technology of inkjet printing, it too is relatively well known. In general, an image is produced by emitting ink drops from an inkjet printhead at precise moments such that they impact a print medium, such as a sheet of paper, at a desired location. The printhead is supported by a movable print carriage within a device, such as an inkjet printer, and is caused to reciprocate relative to an advancing print medium and emit ink drops at such times pursuant to commands of a microprocessor or other controller. The timing of the ink drop emissions corresponds to a pattern of pixels of the image being printed. Other than printers, familiar devices incorporating inkjet technology include fax machines, all-in-ones, photo printers, and graphics plotters, to name a few.

A conventional thermal inkjet printhead includes access to a local or remote supply of color or mono ink, a heater chip, a nozzle or orifice plate attached to the heater chip, and an input/output connector, such as a tape automated bond (TAB) circuit, for electrically connecting the heater chip to the printer during use. The heater chip, in turn, typically includes a plurality of thin film resistors or heaters fabricated by deposition, masking and etching techniques on a substrate such as silicon.

To print or emit a single drop of ink, an individual heater is uniquely addressed with a small amount of current to rapidly heat a small volume of ink. This causes the ink to vaporize in a local ink chamber (between the heater and nozzle plate) and be ejected through and projected by the nozzle plate towards the print medium.

During manufacturing of the printheads, a printhead body gets stuffed with a back pressure device, such as a foam insert, and saturated with mono or color ink. A lid welds to the body via ultrasonic vibration. This, however, sometimes causes cracks in the heater chip, introduces and entrains air bubbles in the ink and compromises overall integrity.

Even further, as demands for higher resolution and increased printing speed continue, heater chips become engineered with more complex and denser heater configurations which raises printhead costs. Simultaneously, the heater chips become smaller and flimsier to save silicon costs. Thus, as printheads evolve, a need exists to control overall costs and to reliably and consistently manufacture a printhead without causing cracking of the ever valuable heater chip.

SUMMARY OF THE INVENTION

The above-mentioned and other problems become solved by applying the principles and teachings associated with the hereinafter described measurement of laser light transmissivity in a to-be-welded region of a work piece.

In one embodiment, the invention teaches methods for measuring laser light transmissivity of a specific position in a work piece prior to the work piece undergoing laser welding at the specific position with a laser beam having a specific welding wavelength. As a first step, the invention teaches obtaining a baseline measurement reading between a laser light source and a detector by projecting a laser beam, at the to-be-welded welding wavelength, directly into the detector. The work piece becomes suspended between the laser light source and detector such that the laser beam at the welding wavelength passes through the work piece in the vicinity of the specific to-be-welded position and into the detector. An output of the detector corresponds to a work piece measurement reading. Differences between the two readings reveal whether the work piece will yield a satisfactory weld at the specific position when later welded by a laser beam at the welding wavelength. The invention also contemplates filters, mirrors, collimators, lenses and the like in the optical path between the light source and the detector.

In another aspect of the invention, a substantially bottomless tray suspends work pieces between the laser light source and the detector such that when the work piece becomes indexed to a new position, the tray never interferes with the beam of laser light. An X-Y motion table in combination with a stepper motor preferably provides the impetus for indexing.

In still another aspect, indexing motion and laser light transmissivity readings occur in patterns substantially paralleling a periphery of the work piece.

Inkjet printhead lids and bodies, laser welded together at specific positions having undergone laser light transmissivity measurements at specific welding wavelengths, and printers containing the printheads are also disclosed.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims.

DETAILED DESCRIPTION OF THE PREFERRED EMBODIMENTS

In the following detailed description of the preferred embodiments, reference is made to the accompanying drawings that form a part hereof, and in which is shown by way of illustration, specific embodiments in which the inventions may be practiced. These embodiments are described in sufficient detail to enable those skilled in the art to practice the invention, and it is to be understood that other embodiments may be utilized and that process or other changes may be made without departing from the scope of the present invention. As a matter of convention herein, direction arrows and lines in-between serve to show interconnections between devices. The following detailed description is, therefore, not to be taken in a limiting sense, and the scope of the present invention is defined only by the appended claims and their equivalents. In accordance with the present invention, we hereinafter describe measurement of laser light transmissivity in a to-be-welded region of a work piece.

Figure 1:
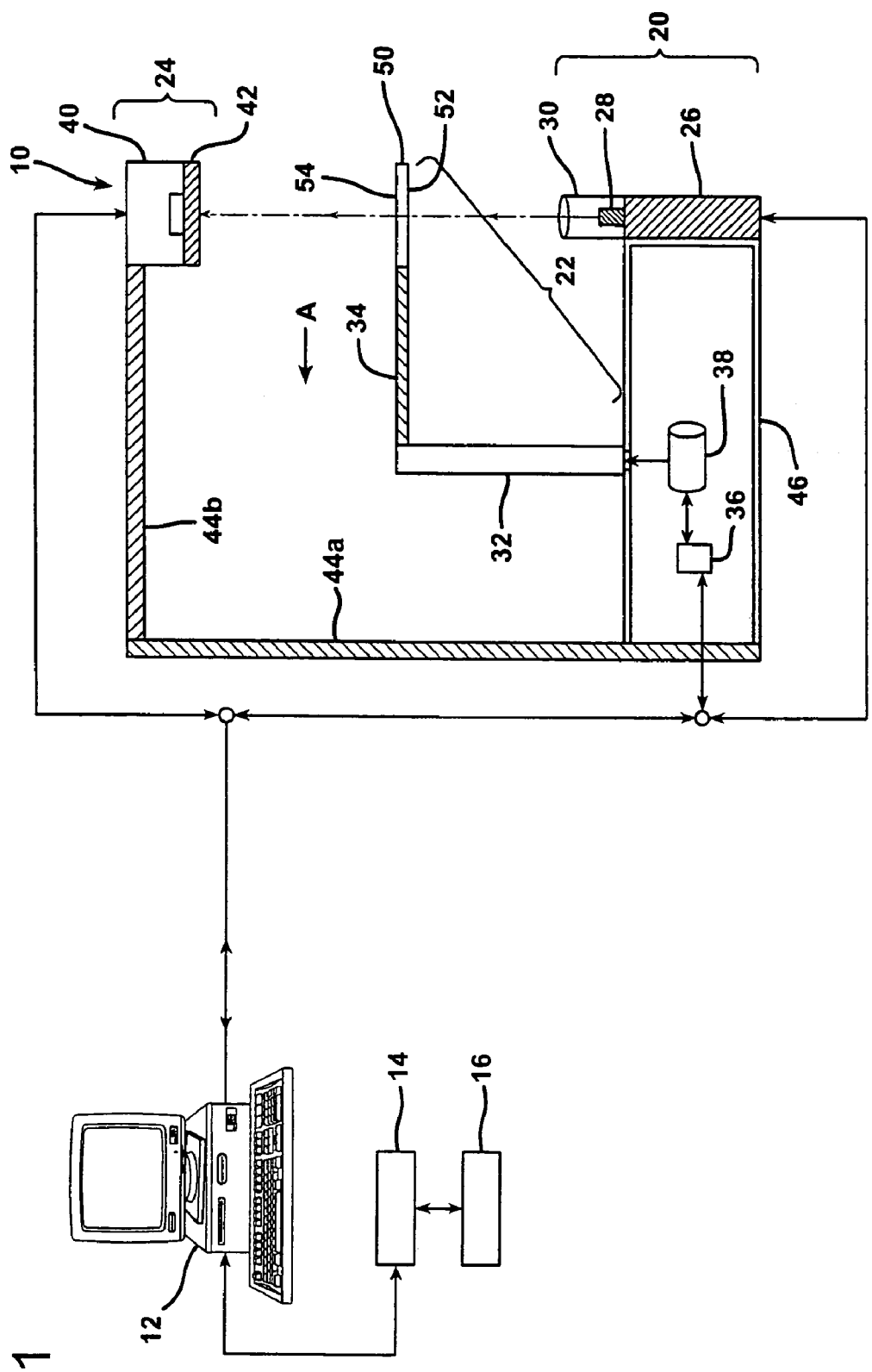
FIG. 1 is a diagrammatic view in accordance with the teachings of the present invention of an apparatus for measuring laser light transmissivity in a to-be-welded region of a work piece.

With reference to FIG. 1, an apparatus for measuring light transmissivity is shown generally as 10. The apparatus includes a computing system environment 12 having, at one end thereof, bi-directional communication with a laser diode power controller 14 and a laser diode temperature controller 16. In a preferred embodiment, the power controller embodies a Thorlabs Inc., LDC2000 2A laser diode controller while the temperature controller embodies a Thorlabs Inc., TEC2000 TEC controller. The computing system environment embodies a general or specific purpose computer with attendant processors, memory, monitors, input devices, network connections, peripheral devices, application programs, connections to intranets and internets and the like.

At the other end, the computing system environment bi-directionally couples with a laser light source structure 20, a motion table 22 and a detector structure 24. In more detail, the laser light source structure 20 includes a laser mount 26, a laser diode 28 and collimating and focusing optics 30. In a preferred embodiment, the laser mount includes a Thorlabs Inc., TCLDM3 TEC LD mount while the diode includes a 1200 mW, T0-3 package from Coherent Laser Diode, S-81-1200C-100-Q. The collimating and focusing optics comprise one or some of Thorlabs Inc.'s: C230TM-B, 600-1500 nm Moderate NA Optics; C260TM-B 600-1500 nm 0.15 NA AR coating; E09 RMS Microscope Objective Adapter Extension Tube; Optics Adapter S1TM09; CP02 Threaded Cage Plate; SM1A3 Microscope Objective to SM1 Adapter; ER4 0876-001 REV B, Extension Rod 4 inch (×4); and SM1RR Retaining Ring. In other embodiments, the laser diode represents an 810 nm wavelength aluminum gallium arsenide (AlGaAs) semiconductor laser having a laser power of about 1000 mW. Still other embodiments include, but are not limited to, other types of continuous wave lasers with similar power intensities such as semiconductor lasers based on Indium Gallium Arsenide (InGaAs) with wavelengths of 940-990 nm and Aluminum Gallium Indium Phosphide (AlGaInP) with wavelengths of 630-680 nm, solid state lasers such as lamp pumped Neodymium-doped Yttrium Aluminum Garnet (Nd:YAG) with a wavelength of 1064 nm and diode pumped Neodymium-doped Yttrium Aluminum Garnet (Nd:YAG) with a wavelength of 1064 nm or solid-state, gas, excimer, dye, ruby or semiconductor lasers or argon fluoride, krypton fluoride, nitrogen, argon (blue or green), helium neon (blue or green), rhodamine 6G dye (tunable), $CrAlO_3$, NIR or carbon dioxide (FIR) laser types or other. The laser diodes of the laser light structure may additionally have labels of class I, I.A, II, IIIA, IIIB, or IV as those are well understood in the art.

The motion table 22 has an elevation arm 32 that allows insertion of a work piece 50 into an optical path (dashed straight line between laser and detector structures) at a position above the laser light source structure. An offset arm 34 of the motion table provides lateral control with motion controlled in a region away (action arrow A) from the optical path. A microcontroller 36 and stepper motor 38 provide the electrical and mechanical impetus to the motion table preferably from instructions originating in the computing system environment. In one embodiment, the motion table 22 has X-Y positioning. In other embodiments, the motion table has X-Y-Z motion, theta motion, angular motion, linear motion or combinations of some or all of the foregoing.

The detector structure 24 includes a photodetector 40 and an optional filter 42. In one embodiment, the photodetector is a Thorlabs Inc., DET 110 350-1100 nm Photodetector while the filter is an NE20A D-2.0 Mounted Absorptive Natural Density Filter.

A support frame 44a, 44b extending from a base 46 provides a platform upon which the laser light source structure 20, the motion table 22 and detector structure 24 commonly connect. In this manner, the frame maintains a common reference point and distances and angles between all structures are known or can be measured. In a preferred embodiment, the frame fixes the laser light source and detector structures relative to one another.

The apparatus 10 may additionally include various mechanical/electrical interlocks (not shown) between any or all of the foregoing structures to meet or exceed federal safety requirements. In one embodiment, the base 46, the frame 44 and all structures connected thereto reside within a light safe enclosure (not shown) according to ANSI standard Z136.1, for example. Other apparatus structures include suitable power sources (not shown) to power some or all of the foregoing.

During use, the apparatus 10 works to emanate and project a laser beam(s) along the optical path from the laser light source structure 20 to a front side 52 of the work piece. In turn, the laser beam(s) passes, or not, through the work piece 50 to a backside 54 and into the detector. Signals output from the detector become transferred to the computing system environment where a user/software analyzes them for light transmissivity characteristics of the work piece.

More specifically, and as a preliminary matter, the work piece 50 is loaded in the tray 70 at a home position, which is around 200 mm away from the laser light source structure 20 and the detector structure 24. A safety door of the light safe enclosure shuts and the apparatus obtains a baseline measurement reading by originating and projecting a laser beam along the optical path in a direct line from the light source structure to the detector structure without passing the laser beam through the work piece.

Thereafter, the work piece 50 is inserted into the optical path by movement from the home position to a starting position between the laser light source and detector structures by the X-Y motion table. The laser beam projects toward/through the work piece and light collected from the backside 54 by the detector corresponds to a work piece measurement reading. This process repeats, as described in greater detail below, such that pluralities of work piece measurement readings are obtained. Differences between the baseline measurement and the work piece measurement readings reveal the laser light transmissivity of the work piece. In a preferred embodiment, voltage outputs of the detector structure 24 have a mathematical relationship in terms of transmitted light T(t) such that $T(t)=Y(t)/X$; where Y is the detected intensity at time t and X is the baseline measurement reading. A mean transmissivity value can be calculated by summing the above equation for the duration of a given time interval.

Figure 4:
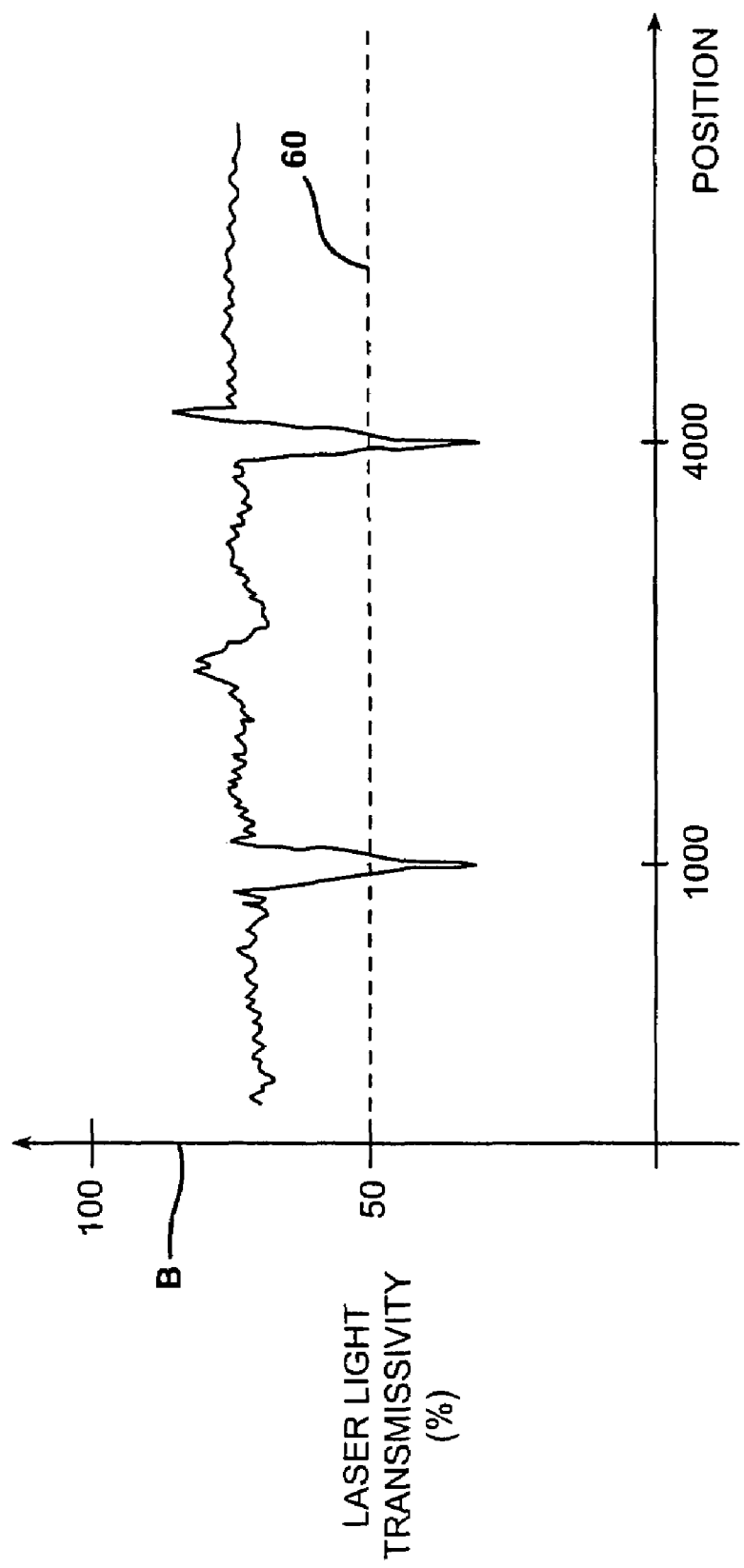
FIG. 4 is a graph in accordance with the teachings of the present invention of measured laser light transmissivity of a work piece plotted against discrete measurement positions.

As an example, consider a baseline measurement reading having some trivial output of about 10 volts. Next consider a first work piece measurement reading of about 7 volts. In percentages, the laser light transmissivity of the work piece at that work piece position is about 70%. Then, as additional work piece measurement readings are taken, preferably at other work piece positions, information about the work piece transmissivity is obtained and can be graphed as shown representatively in FIG. 4.

As readily identifiable in the graph, laser light transmissivity preferably stays within a zone B between 50 and 100 percent, for example. Yet, at measurement positions 1000 and 4000, laser light transmissivity drops to much lower percentage levels. Over time, and from knowledge learned by testing and identifying acceptable laser welds of work pieces, users can set some minimum acceptable level, such as dashed line 60, that readily identifies whether the work piece under test in apparatus 10 will yield satisfactory weld results. Users will set their own criteria for distinguishing satisfactory welds from unsatisfactory ones. The criteria may include, but are not limited to, how many aberrations such as those found at positions 1000/4000 a weld can withstand or how high a laser light transmissivity percentage on average, total, or other will yield an acceptable result. For thorough disclosure, the representative readings taken at work piece measurement positions 1000 and 4000 were found in one actual reduction to practice to correspond to impurities, such as carbon or steel, in the composition of the work piece in instances when the work piece comprised a plastic formed in an injection molding chamber.

It should be appreciated, however, that testing the work piece in apparatus 10 (FIG. 1) for transmissivity characteristics is performed at a laser wavelength corresponding substantially to the specific laser wavelength used during laser welding. Even more preferably, testing of the work pieces in apparatus 10 occurs with the same exact laser light source structure 20 used during subsequent laser welding operations of the work piece. In this manner, users can even more accurately predict and identify a direct correlation between transmissivity and satisfactory welds.

Figure 2A:
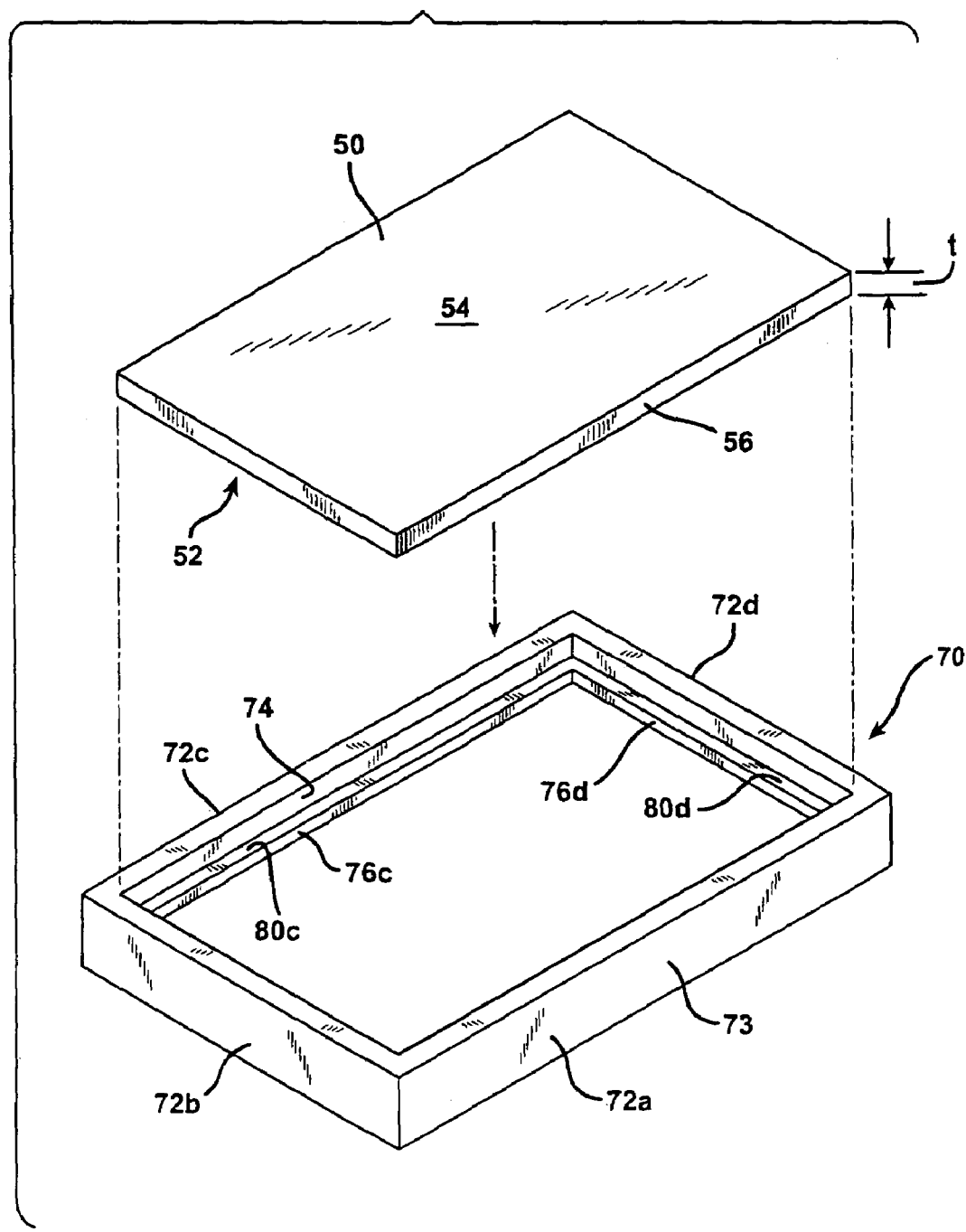
FIG. 2A is a diagrammatic view in accordance with the teachings of the present invention of a tray for suspending a work piece between a laser light source and a detector for use with the apparatus of FIG. 1.
Figure 2B:
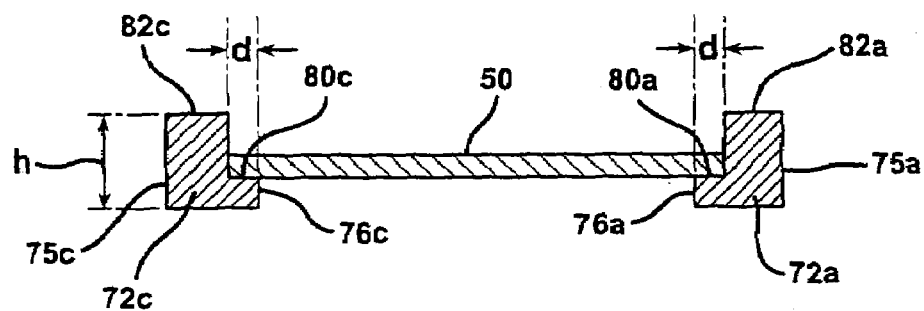
FIG. 2B is a cross-section view in accordance with the teachings of the present invention of the to-be-welded work piece of FIG. 2A after being placed in the tray.

To physically introduce the work piece between the laser light source and detector structures, the offset arm 34 having the work piece 50 therewith rotates or otherwise moves into the optical path. With reference to FIGS. 2A and 2B, a preferred structure for holding the work piece at a terminal end of the offset arm includes a tray 70.

As shown, the tray 70 has a plurality of walls 72(a-d) that form a frame around a periphery 56 of the work piece 50. A perimeter distance of an interior 74 of the walls is slightly larger than the perimeter distance of the periphery 56. In this manner, a user may easily insert the work piece into the tray and the tray will maintain the work piece in a fixed position relative thereto. Near a bottom 75(a-d) of the walls, a ledge 76(a-d) juts out slightly such that when the work piece is inserted into the tray, the front side 52 surface of the work piece rests in contact on a top surface 80(a-d) thereof. In one embodiment, the ledge juts out a distance d of about $5/1000^{th}$ of an inch.

Those skilled in the art should observe that despite a slight ledge, the tray otherwise has a substantially bottomless quality. In this manner, when the laser light source structure 20 (FIG. 1) projects laser beams of light towards, and perhaps through the work piece, the substantially bottomless tray 70 suspends the work piece between the laser light source and detector structures such that nearly the entirety of the front side 52 surface of the work piece receives direct laser light without any interference from the tray. Preferably, in a direct line (e.g., optical path, dashed line, FIG. 1) between the laser light source structure 20 and the detector structure 24, no portion of the tray ever crosses the line.

The tray 70 can affix to the offset arm at any variety of positions, such as outside 73 of wall 72a, by adhesives, clamps, fasteners or other or by integral formation therewith.

As depicted, the work piece 50 has a thickness t less than a height h of the walls so that it nests within the tray. Those skilled in the art will appreciate, however, that the work piece may have other thicknesses that extend beyond or exist substantially parallel to a top 82(a-d) of the walls and this invention embraces all varieties.

Figure 2C:
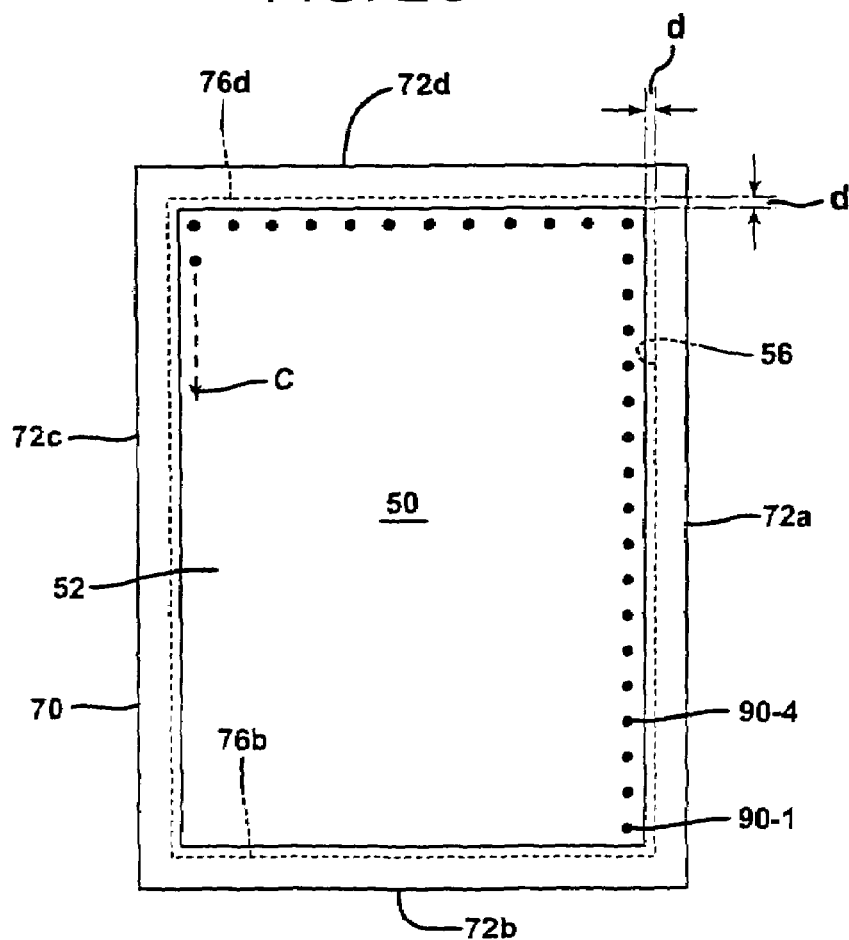
FIG. 2C is a planar view in accordance with the teachings of the present invention of the to-be-welded work piece held in the tray of FIG. 2B having pluralities of laser light transmissivity measurement positions indicated.

To have even greater usefulness, the positions, in which transmissivity measurements are taken, should correspond directly to the positions that will later become laser welded. With reference to FIG. 2C, a plurality of such later-welded work piece positions are shown generally as a plurality of discrete dots (with two labeled 90-1 and 90-4) arranged in a substantially rectangular pattern (although only shown on three sides of the work piece 50 with a dashed line arrow C indicating continuation of the pattern) substantially paralleling a periphery 56 of the work piece. Thus, when users take measurements they do so at the positions indicated by the pattern.

The invention, however, should not be considered so narrowly to preclude other patterns of work piece positions. Thus, the invention contemplates other patterns and user need generally dictates them. For example, the invention finds equal utility with round, triangular, square, linear, spotted and random or other patterns or patterns of continual lines of positions instead of discrete positions or combinations thereof.

In one actual embodiment, the invention found utility with about 12,000 work piece positions in a substantially rectangular pattern with about $\frac{1}{2}$ of $1/10000^{th}$ of an inch between positions. The measurements occurred at the work piece positions in the following manner: i) introduce and suspend the work piece in the tray at a home position away from the optical path; ii) project a laser beam directly from the light source to the detector structure; iii) obtain a baseline measurement reading; (iv) energize stepping motor to stepwise control movement of the tray and work piece to the starting position between the light source and detector structures directly in the optical path; v) obtain a work piece measurement reading by passing the laser beam (which is continuous on, but not necessarily required to be) from the light source structure into the work piece and observing/recording the output of the detector structure; (vi) energize the stepping motor to stepwise control movement of the tray; (vii) index the tray 70 and work piece 50 such that the next work piece position is in the optical path; (viii) repeat steps (v)-(viii) until an entirety of the work piece is measured; ix) stop the laser beam from projecting; and x) return tray 70 and work piece to the home position by indexing the stepping motor. The work piece embodied a substantially rectangular solid plastic composition of Noryl Brand TN 300 having a thickness of about 2 mm and a length and width of about 50 mm and 25 mm, respectively.

Figure 3:
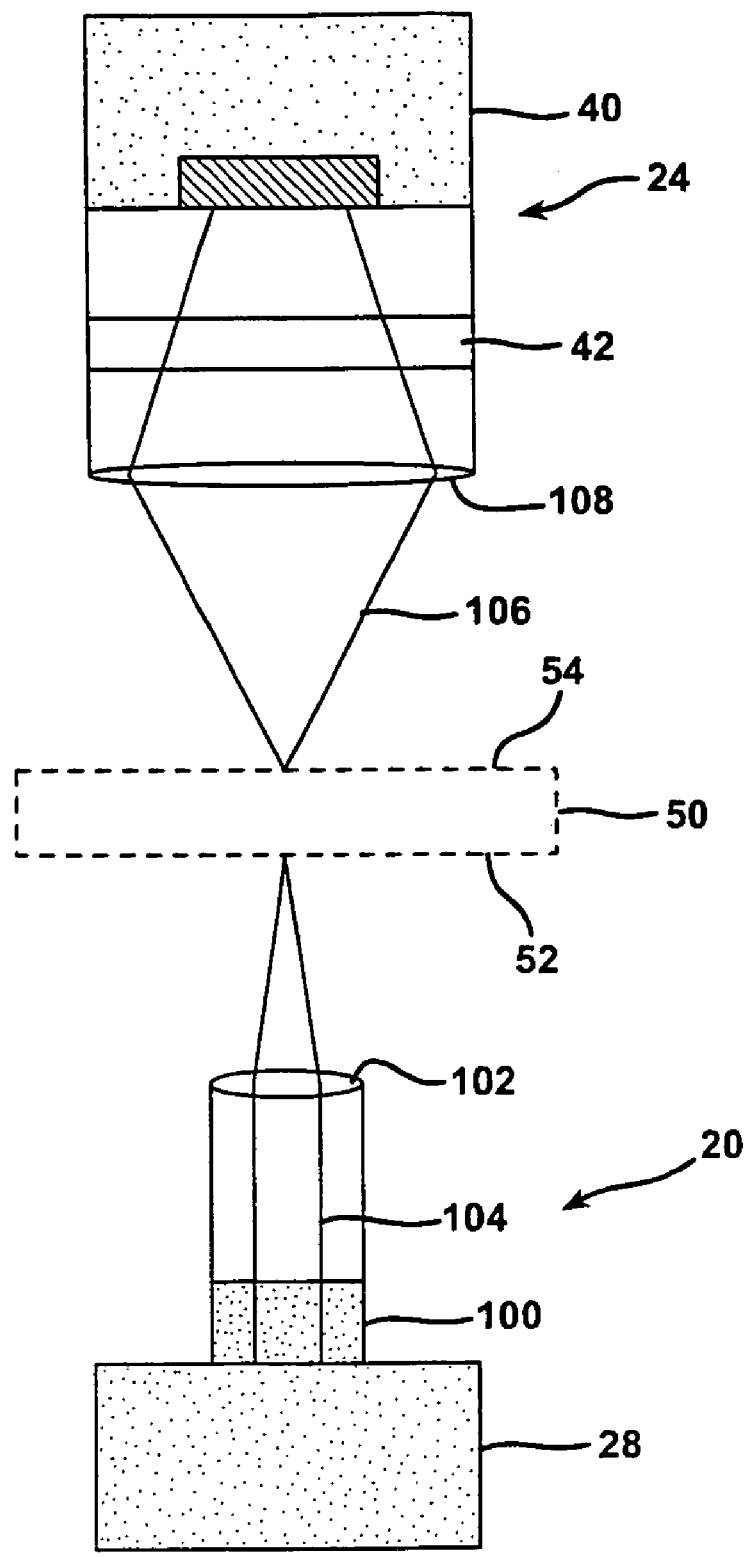
FIG. 3 is a diagrammatic view in accordance with the teachings of the present invention of laser light projected through a work piece and collected by a detector for use with the apparatus of FIG. 1.

With reference to FIG. 3, the invention presents a more detailed illustration of a preferred optical path for use in the apparatus 10 of FIG. 1. In particular, laser diode 28 in combination with a collimating lens 100 and focusing lens 102 projects a laser beam 104 from the laser light source structure towards a front side 52 of the work piece 50. The detector structure collects transmitted laser light 106 from a back side 54 of the work piece with assistance from a converging lens 108, filter 42 and photodetector 40. In other embodiments, the optical path optionally includes additional lenses, filters collimators or other optical elements, such as mirrors, fiber optic strands, scanning structures or the like.

Finally, since the invention herein contemplates the work piece as an inkjet printhead lid or body, the remaining description relates to specific work piece compositions and their arrangement as part of a laser welded printhead lid/body.

Figure 5:
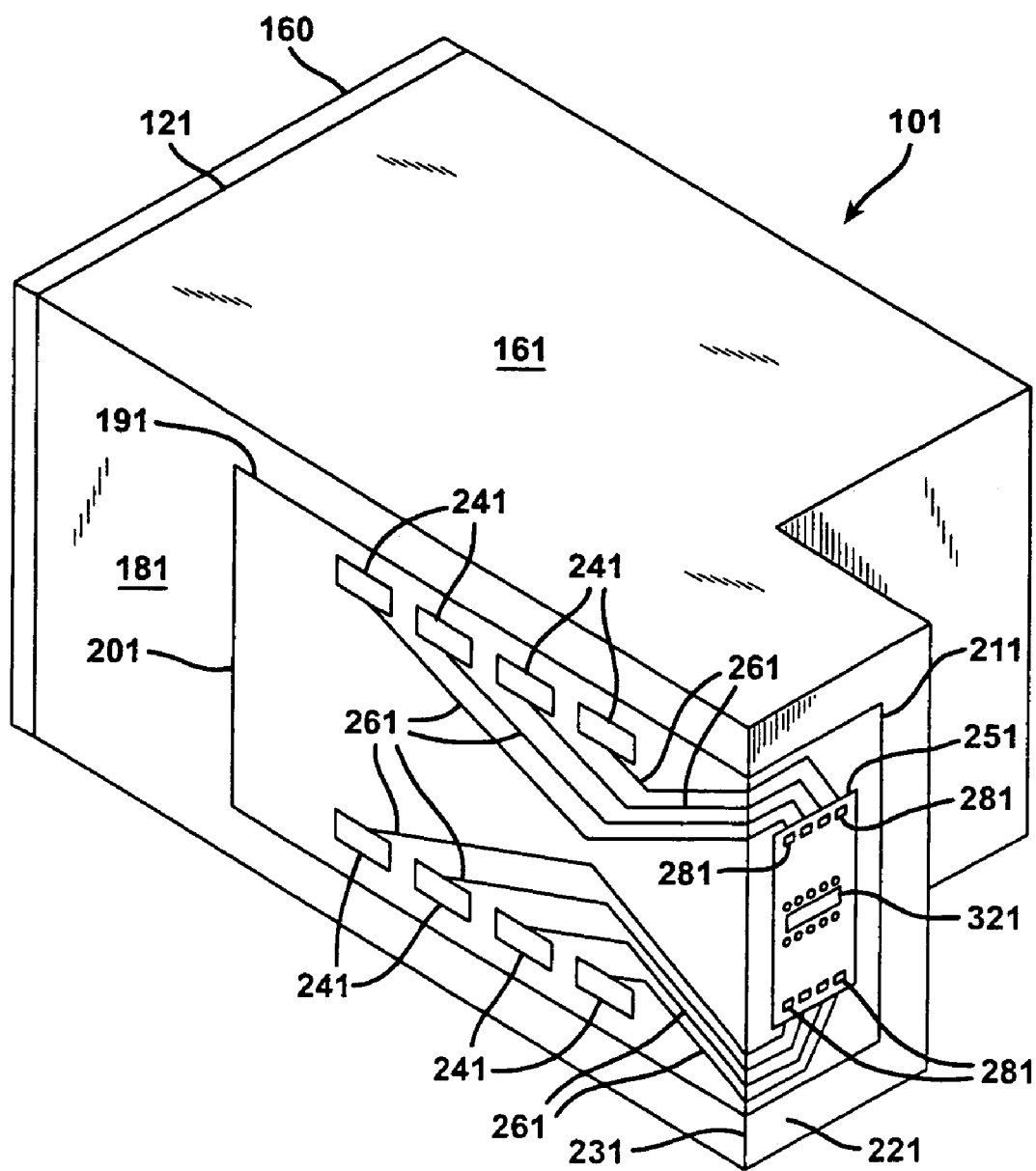
FIG. 5 is a perspective view in accordance with the teachings of the present invention of an inkjet printhead with a laser light transmissivity measured inkjet lid laser welded to an inkjet body.

With reference to FIG. 5, a printhead of the present invention is shown generally as 101. The printhead 101 has a housing 121 formed of a body 161 and a lid 160 laser welded together by a laser beam at a welding laser wavelength at a specific work piece position at a time after the lid has its work piece position measured for laser light transmissivity at the specified welding laser wavelength. In one preferred embodiment, the lid comprises a laser transparent material having a composition of polyphenylene ether plus polystyrene while the body comprises a laser absorbing material also having a composition of polyphenylene ether plus polystyrene. Although shown generally as a rectangular solid, the housing shape varies and depends upon the external device that carries or contains the printhead. The housing has at least one compartment, internal thereto, for holding an initial or refillable supply of ink and a structure, such as a foam insert, lung or other, for maintaining appropriate backpressure in the inkjet printhead during use. In one embodiment, the internal compartment includes three chambers for containing three supplies of ink, especially cyan, magenta and yellow ink. In other embodiments, the compartment may contain black ink, photo-ink and/or plurals of cyan, magenta or yellow ink. It will be appreciated that fluid connections (not shown) may exist to connect the compartment(s) to a remote source of ink.

A portion 191 of a tape automated bond (TAB) circuit 201 adheres to one surface 181 of the housing while another portion 211 adheres to another surface 221. As shown, the two surfaces 181, 221 exist perpendicularly to one another about an edge 231.

The TAB circuit 201 has a plurality of input/output (I/O) connectors 241 fabricated thereon for electrically connecting a heater chip 251 to an external device, such as a printer, fax machine, copier, photo-printer, plotter, all-in-one, etc., during use. Pluralities of electrical conductors 261 exist on the TAB circuit 201 to electrically connect and short the I/O connectors 241 to the bond pads 281 of the heater chip 251 and various manufacturing techniques are known for facilitating such connections. It will be appreciated that while eight I/O connectors 241, eight electrical conductors 261 and eight bond pads 281 are shown, any number are embraced herein. It is also to be appreciated that such number of connectors, conductors and bond pads may not be equal to one another.

The heater chip 251 contains at least one ink via 321 that fluidly connects to a supply of ink internal to the housing. During printhead manufacturing, the heater chip 251 preferably attaches to the housing with any of a variety of adhesives, epoxies, etc. well known in the art. As shown, the heater chip contains two columns of heaters on either side of via 321. For simplicity in this crowded figure, dots depict the heaters in the columns. It will be appreciated that the heaters of the heater chip preferably become formed as a series of thin film layers made via growth, deposition, masking, photolithography and/or etching or other processing steps. A nozzle plate with pluralities of nozzle holes, not shown, adheres over the heater chip such that the nozzle holes align with the heaters.

Figure 6:
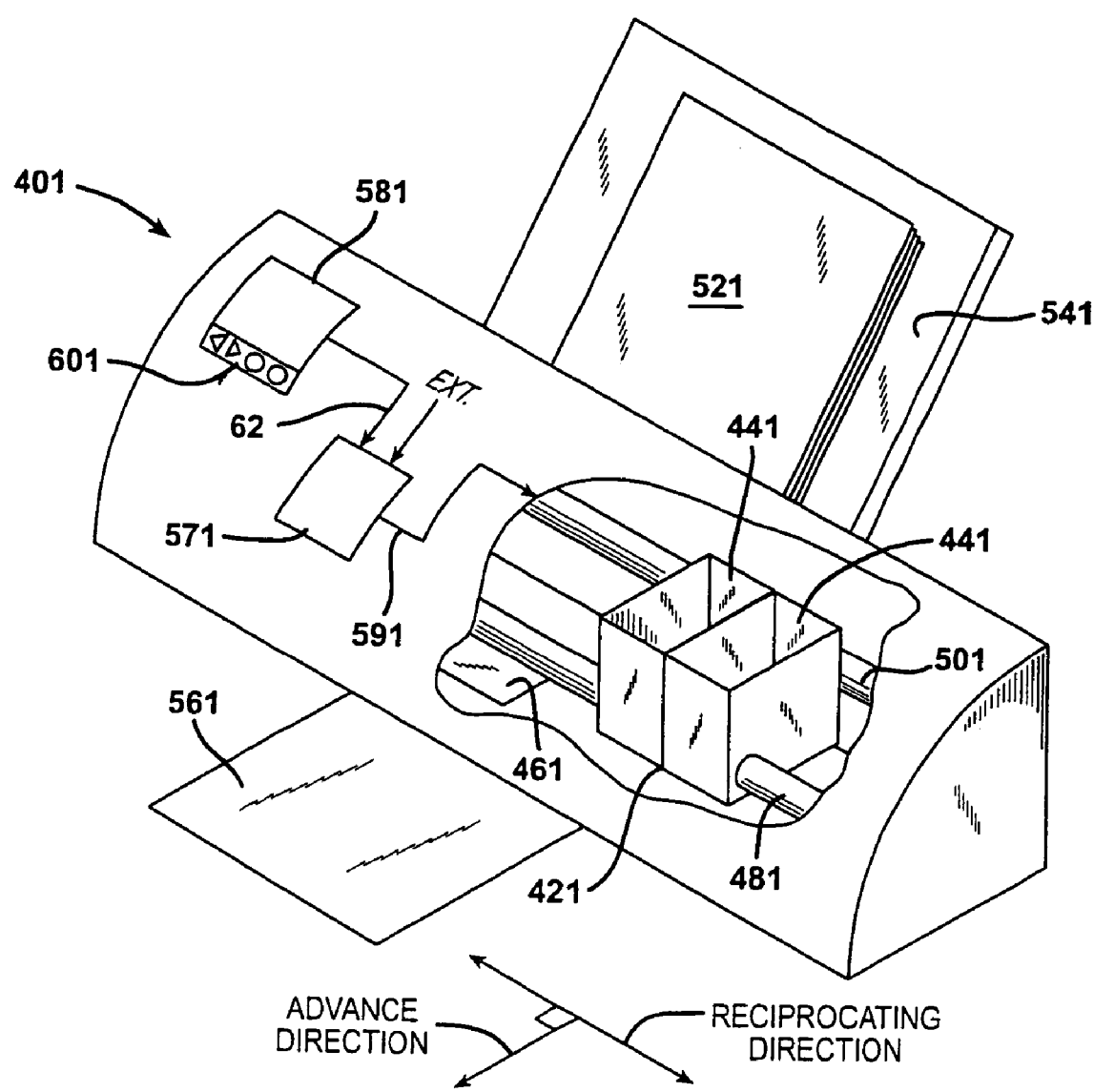
FIG. 6 is a perspective view in accordance with the teachings of the present invention of an inkjet printer for housing an inkjet printhead with a laser light transmissivity measured inkjet lid laser welded to an inkjet body.

With reference to FIG. 6, an external device, in the form of an inkjet printer, for containing the printhead 101 is shown generally as 401. The printer 401 includes a carriage 421 having a plurality of slots 441 for containing one or more printheads. The carriage 421 is caused to reciprocate (via an output 591 of a controller 571) along a shaft 481 above a print zone 461 by a motive force supplied to a drive belt 501 as is well known in the art. The reciprocation of the carriage 421 is performed relative to a print medium, such as a sheet of paper 521, that is advanced in the printer 401 along a paper path from an input tray 541, through the print zone 461, to an output tray 561.

In the print zone, the carriage 421 reciprocates in the Reciprocating Direction generally perpendicularly to the paper Advance Direction as shown by the arrows. Ink drops from the printheads (FIG. 5) are caused to be ejected from the heater chip at such times pursuant to commands of a printer microprocessor or other controller 571. The timing of the ink drop emissions corresponds to a pattern of pixels of the image being printed. Often times, such patterns are generated in devices electrically connected to the controller (via Ext. input) that are external to the printer such as a computer, a scanner, a camera, a visual display unit, a personal data assistant, or other.

To print or emit a single drop of ink, the heaters (the dots of FIG. 5) are uniquely addressed with a small amount of current to rapidly heat a small volume of ink. This causes the ink to vaporize in a local ink chamber and be ejected through, and projected by, a nozzle plate towards the print medium.

A control panel 581 having user selection interface 601 may also provide input 621 to the controller 571 to enable additional printer capabilities and robustness.

As described herein, the term inkjet printhead may in addition to thermal technology include piezoelectric technology, or other, and may embody a side-shooter structure instead of the head-shooter structure shown. Finally, since the to-be-welded work piece described above may embody an inkjet printhead lid and/or body and since laser welding imparts essentially no vibratory motion in the work pieces, unlike ultrasonic welding, less cracking of the heater chip occurs and less air becomes entrained in the ink during printhead manufacturing.

The foregoing description is presented for purposes of illustration and description of the various aspects of the invention. The descriptions are not intended to be exhaustive or to limit the invention to the precise form disclosed. The embodiments described above were chosen to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for measuring laser light transmissivity before laser welding, comprising:
   introducing a work piece that is to undergo laser welding at a specific laser wavelength a work piece position between a laser light source and a detector;
   without cutting or welding said work piece, passing a laser beam at said wavelength from said laser light source through said work piece in a vicinity of said work piece position and into said detector to obtain a work piece measurement reading; and
   based upon said reading, assessing whether said work piece will satisfactorily undergo subsequent laser welding to another work piece at said work piece position at said wavelength.

2. The method of claim 1, further including stepwise controlling movement of said work piece between said laser light source and said detector.

3. The method of claim 1, further including projecting said laser beam at said wavelength from said laser light source into said detector without passing through said work piece to obtain a baseline measurement reading.

4. The method of claim 1, wherein said introducing further includes suspending said work piece between said laser light source and said detector.

5. The method of claim 4, wherein said suspending further includes positioning said work piece in a substantially bottomless tray.

6. The method of claim 1, further including laser welding said work piece to an inkjet printhead body at said work piece position.

7. The method of claim 1, wherein said assessing further includes plotting said measurement reading versus said work piece position.

8. The method of claim 1, wherein said assessing further includes determining whether said measurement reading is above a predetermined minimum acceptable level.

9. A method for measuring laser light transmissivity in a work piece before laser welding said work piece to another work piece, comprising:

introducing said work piece that is to undergo laser welding at a specific laser wavelength at a plurality of work piece positions in an optical path between a laser light source and a detector;

without cutting or welding said work piece, passing a laser beam at said wavelength through said work piece in a vicinity of said work piece positions to obtain a plurality of work piece measurement readings; and based upon said measurement readings, assessing whether said work piece will satisfactorily undergo subsequent laser welding to said another work piece at said work piece positions at said wavelength.

10. The method of claim 9, further including stepwise controlling movement of said work piece between said laser light source and said detector.

11. The method of claim 9, wherein said passing said laser beam further includes repeatedly and discretely passing a beam of laser light through said work piece.

12. The method of claim 9, wherein said passing said laser beam further includes continually passing a beam of laser light through said work piece.

13. The method of claim 9, further including projecting said laser beam at said wavelength from said laser light source into said detector without passing through said work piece to obtain a baseline measurement reading.

14. The method of claim 9, wherein said assessing further includes plotting said measurement readings versus said work piece positions.

15. The method of claim 14, wherein said assessing further includes determining whether a sufficient percentage of said measurement readings are above a predetermined minimum acceptable level.

* * * * *